(12) United States Patent
Douglas et al.

(10) Patent No.: US 11,275,242 B1
(45) Date of Patent: Mar. 15, 2022

(54) METHOD AND APPARATUS FOR PERFORMING STEREOSCOPIC ROTATION OF A VOLUME ON A HEAD DISPLAY UNIT

(71) Applicants: Robert Edwin Douglas, Winter Park, FL (US); David Byron Douglas, Winter Park, FL (US)

(72) Inventors: Robert Edwin Douglas, Winter Park, FL (US); David Byron Douglas, Winter Park, FL (US)

(73) Assignee: TIPPING POINT MEDICAL IMAGES, LLC, Winter Park, FL (US)

( * ) Notice: Subject to any disclaimer, the term of this patent is extended or adjusted under 35 U.S.C. 154(b) by 0 days.

(21) Appl. No.: 17/459,011

(22) Filed: Sep. 26, 2021

Related U.S. Application Data

(63) Continuation-in-part of application No. 16/506,073, filed on Jul. 9, 2019, now Pat. No. 11,202,061, which is a continuation-in-part of application No. 15/878,463, filed on Jan. 24, 2018, now Pat. No. 10,795,457, which is a continuation-in-part of application No. 14/877,442, filed on Oct. 7, 2015, now Pat. No. 9,980,691, which is a continuation-in-part of application No. 12/176,569,
(Continued)

(51) Int. Cl.
| | |
|---|---|
| *H04N 7/18* | (2006.01) |
| *G02B 27/01* | (2006.01) |
| *A61B 5/026* | (2006.01) |
| *G02B 30/22* | (2020.01) |
| *G02B 30/54* | (2020.01) |

(52) U.S. Cl.
CPC ......... *G02B 27/0101* (2013.01); *A61B 5/026* (2013.01); *G02B 30/22* (2020.01); *G02B 30/54* (2020.01)

(58) Field of Classification Search
CPC ................................................. G02B 27/0101
USPC .......................................................... 348/53
See application file for complete search history.

(56) References Cited

U.S. PATENT DOCUMENTS

| | | |
|---|---|---|
| 4,472,737 A | 9/1984 | Iwasaki |
| 4,808,979 A | 2/1989 | DeHoff et al. |
| (Continued) | | |

FOREIGN PATENT DOCUMENTS

| | | |
|---|---|---|
| CN | 1885233 A | 12/2006 |
| CN | 102968791 A | 3/2013 |
| (Continued) | | |

OTHER PUBLICATIONS

Notice of Allowance for U.S. Appl. No. 17/021,548 dated Jan. 13, 2021.
(Continued)

*Primary Examiner* — Leron Beck

(57) ABSTRACT

Pointers are added to a 3D volumetric dataset to help the user visualize the direction of blood flow. A 3D volume containing at least one blood vessel is created. Next, the direction of the blood flow is determined. Next, at least pointer is placed into the 3D volume in an aligned fashion with the direction of blood flow such that the 3D volume is modified. Next, the modified 3D volume is displayed on a head display unit, such as an augmented reality or virtual reality display. Next, at least one pointer is advanced to a new position for additional modification of the 3D imaging volume.

21 Claims, 6 Drawing Sheets

Related U.S. Application Data filed on Jul. 21, 2008, now Pat. No. 9,349,183, which is a continuation-in-part of application No. 11/941,578, filed on Nov. 16, 2007, now Pat. No. 8,384,771.

(60) Provisional application No. 60/877,931, filed on Dec. 28, 2006.

(56) References Cited

U.S. PATENT DOCUMENTS

| | | |
|---|---|---|
| 4,870,600 A | 9/1989 | Hiraoka |
| 4,871,233 A | 10/1989 | Sheiman |
| 4,952,024 A | 4/1990 | Gale |
| 4,896,210 A | 6/1990 | Brokenshire et al. |
| 4,987,527 A | 1/1991 | Hamada |
| 5,049,987 A | 9/1991 | Hoppenstein |
| 5,113,285 A | 5/1992 | Franklin et al. |
| 5,162,897 A | 11/1992 | Jitsukata et al. |
| 5,200,819 A | 4/1993 | Nudelman et al. |
| 5,233,458 A | 8/1993 | Moffitt et al. |
| 5,278,884 A | 1/1994 | Eberhard et al. |
| 5,293,529 A | 3/1994 | Yoshimura et al. |
| 5,371,778 A | 12/1994 | Yanof et al. |
| 5,402,191 A | 5/1995 | Dean et al. |
| 5,488,952 A | 2/1996 | Schoolman |
| 5,493,595 A | 2/1996 | Schoolman |
| 5,510,832 A | 4/1996 | Garcia |
| 5,523,886 A * | 6/1996 | Johnson-Williams ......................... A63F 13/02 359/464 |
| 5,524,187 A | 6/1996 | Feiner et al. |
| 5,535,747 A * | 7/1996 | Katakura .................. A61B 8/04 600/438 |
| 5,541,641 A | 7/1996 | Shimada |
| 5,564,810 A | 10/1996 | Larson |
| 5,566,280 A | 10/1996 | Fukui et al. |
| 5,621,867 A | 4/1997 | Murata et al. |
| 5,627,582 A | 5/1997 | Muramoto et al. |
| 5,644,324 A | 7/1997 | Maguire, Jr. |
| 5,659,625 A | 8/1997 | Marquardt |
| 5,682,172 A | 10/1997 | Travers et al. |
| 5,682,437 A | 10/1997 | Okino et al. |
| 5,696,521 A | 12/1997 | Robinson et al. |
| 5,708,359 A | 1/1998 | Gregory et al. |
| 5,714,997 A | 2/1998 | Anderson |
| 5,734,416 A | 3/1998 | Ito et al. |
| 5,745,163 A | 4/1998 | Nakamura et al. |
| 5,822,117 A | 10/1998 | Kleinberger et al. |
| 5,841,830 A | 11/1998 | Barni et al. |
| 5,850,352 A | 12/1998 | Moezzi et al. |
| 5,852,646 A | 12/1998 | Klotz et al. |
| 5,867,588 A | 2/1999 | Marquardt |
| 5,875,055 A * | 2/1999 | Morishima ............ G02B 30/27 359/465 |
| 5,880,883 A | 3/1999 | Sudo |
| 5,978,143 A | 11/1999 | Spruck |
| 5,986,662 A | 11/1999 | Argiro et al. |
| 5,993,004 A | 11/1999 | Moseley et al. |
| 5,999,165 A | 12/1999 | Matsumoto |
| 6,002,518 A | 12/1999 | Faris |
| 6,034,716 A | 3/2000 | Whiting et al. |
| 6,052,100 A | 4/2000 | Soltan et al. |
| 6,057,827 A | 5/2000 | Matthews |
| 6,066,095 A | 5/2000 | Morsy et al. |
| 6,084,937 A | 7/2000 | Tam et al. |
| 6,100,862 A | 8/2000 | Sullivan |
| 6,108,005 A * | 8/2000 | Starks .................... G02B 30/24 345/419 |
| 6,115,449 A | 9/2000 | Jang et al. |
| 6,124,977 A | 9/2000 | Takahashi |
| 6,130,930 A | 10/2000 | Tam |
| 6,191,808 B1 | 2/2001 | Katayama et al. |
| 6,201,566 B1 | 3/2001 | Harada et al. |
| 6,211,884 B1 | 4/2001 | Knittel et al. |
| 6,211,927 B1 | 4/2001 | Yamazaki et al. |
| 6,220,709 B1 | 4/2001 | Heger |
| 6,225,979 B1 | 5/2001 | Taima et al. |
| 6,252,707 B1 | 6/2001 | Kleinberger et al. |
| 6,272,366 B1 | 8/2001 | Vining |
| 6,275,561 B1 | 8/2001 | Danielsson |
| 6,276,799 B1 | 8/2001 | Van Saarloos et al. |
| 6,297,799 B1 | 10/2001 | Knittel et al. |
| 6,342,378 B1 | 1/2002 | Zhang et al. |
| 6,342,878 B1 | 1/2002 | Chevassus et al. |
| 6,346,940 B1 | 2/2002 | Fukunaga |
| 6,377,230 B1 | 4/2002 | Yamazaki et al. |
| 6,407,737 B1 | 6/2002 | Zhao et al. |
| 6,429,861 B1 | 8/2002 | Hossack et al. |
| 6,429,884 B1 | 8/2002 | Budz et al. |
| 6,442,417 B1 | 8/2002 | Shahidi et al. |
| 6,449,005 B1 | 9/2002 | Faris |
| 6,449,090 B1 | 9/2002 | Omar et al. |
| 6,449,309 B1 | 9/2002 | Tabata |
| 6,466,185 B2 | 10/2002 | Sullivan et al. |
| 6,476,607 B1 | 11/2002 | Dannels et al. |
| 6,487,432 B2 | 11/2002 | Slack |
| 6,490,335 B1 | 12/2002 | Wang et al. |
| 6,501,468 B1 * | 12/2002 | Kaji ..................... G06T 15/10 345/419 |
| 6,507,359 B1 | 1/2003 | Muramoto et al. |
| 6,532,008 B1 | 3/2003 | Guralnick |
| 6,545,650 B1 | 4/2003 | Yamada et al. |
| 6,549,803 B1 | 4/2003 | Raghavan et al. |
| 6,570,629 B1 | 5/2003 | Hirakata et al. |
| 6,580,448 B1 | 6/2003 | Stuttler |
| 6,606,091 B2 | 8/2003 | Liang et al. |
| 6,608,628 B1 | 8/2003 | Ross et al. |
| 6,676,259 B1 | 1/2004 | Trifilo |
| 6,692,441 B1 | 2/2004 | Poland et al. |
| 6,711,231 B2 | 3/2004 | Knoplioch et al. |
| 6,734,847 B1 | 5/2004 | Baldeweg et al. |
| 6,762,794 B1 | 7/2004 | Ogino |
| 6,792,071 B2 | 9/2004 | Dewaele |
| 6,798,412 B2 | 9/2004 | Cowperthwaite |
| 6,847,336 B1 * | 1/2005 | Lemelson ............. G16H 20/40 345/8 |
| 6,862,364 B1 | 3/2005 | Berestov |
| 6,885,886 B2 | 4/2005 | Bauch et al. |
| 6,947,039 B2 | 9/2005 | Gerritsen et al. |
| 7,002,619 B1 | 2/2006 | Dean et al. |
| 7,020,236 B2 | 3/2006 | Shechter |
| 7,058,156 B2 | 6/2006 | Bruder et al. |
| 7,113,186 B2 | 9/2006 | Kim et al. |
| RE39,342 E | 10/2006 | Starks et al. |
| 7,127,091 B2 | 10/2006 | Op De Beek et al. |
| 7,187,420 B2 | 3/2007 | Yamazaki et al. |
| 7,190,825 B2 | 3/2007 | Yoon et al. |
| 7,193,626 B2 | 3/2007 | Otani et al. |
| 7,193,773 B2 | 3/2007 | Haisch et al. |
| 7,242,402 B1 | 7/2007 | Betting et al. |
| 7,298,372 B2 | 11/2007 | Pfister et al. |
| 7,301,510 B2 | 11/2007 | Hewitt et al. |
| 7,321,682 B2 | 1/2008 | Tooyama et al. |
| 7,324,085 B2 | 1/2008 | Balakrishnan et al. |
| 7,466,336 B2 | 12/2008 | Regan et al. |
| 7,479,933 B2 | 1/2009 | Weissman |
| 7,524,053 B2 | 4/2009 | Lipton |
| 7,604,597 B2 | 10/2009 | Murashita et al. |
| 7,605,776 B2 | 10/2009 | Satoh et al. |
| 7,643,025 B2 | 1/2010 | Lange |
| 7,647,593 B2 | 1/2010 | Matsumoto |
| 7,654,826 B2 | 2/2010 | Faulkner et al. |
| 7,715,608 B2 | 5/2010 | Vaz et al. |
| 7,773,074 B2 | 8/2010 | Arenson et al. |
| 7,786,990 B2 | 8/2010 | Wegenkitt et al. |
| 7,796,790 B2 | 9/2010 | McNutt et al. |
| 7,808,449 B2 | 10/2010 | Neidrich et al. |
| 7,822,265 B2 | 10/2010 | Berretty |
| 7,832,869 B2 | 11/2010 | Maximus et al. |
| 7,840,047 B2 | 11/2010 | Böing et al. |
| 7,907,167 B2 | 3/2011 | Vesely et al. |
| 7,957,061 B1 | 6/2011 | Connor |
| 8,049,773 B2 | 11/2011 | Ishikawa et al. |
| 8,078,000 B2 | 12/2011 | Böhm et al. |

(56) References Cited

U.S. PATENT DOCUMENTS

| | | |
|---|---|---|
| 8,159,526 B2 | 4/2012 | Sato et al. |
| 8,160,341 B2 | 4/2012 | Peng et al. |
| 8,165,365 B2 | 4/2012 | Bernard et al. |
| 8,175,683 B2 | 5/2012 | Roose |
| 8,199,168 B2 | 6/2012 | Virtue |
| 8,228,327 B2 | 7/2012 | Hendrickson et al. |
| 8,233,103 B2 | 7/2012 | MacNaughton et al. |
| 8,248,458 B2 | 8/2012 | Schowengerdt et al. |
| 8,289,380 B2 | 10/2012 | Kim et al. |
| 8,363,096 B1 | 1/2013 | Aguirre |
| 8,384,771 B1 * | 2/2013 | Douglas ............... H04N 13/344 348/53 |
| 8,398,541 B2 | 3/2013 | DiMaio et al. |
| 8,480,234 B2 | 7/2013 | Richards |
| 8,508,583 B2 | 8/2013 | Goto |
| 8,520,024 B2 | 8/2013 | Guthrie et al. |
| 8,542,326 B2 | 9/2013 | MacNaughton et al. |
| 8,547,422 B2 | 10/2013 | Surman |
| 8,565,505 B2 | 10/2013 | Bergmans et al. |
| 8,567,954 B2 | 10/2013 | Koehler et al. |
| D692,941 S | 11/2013 | Klinar et al. |
| 8,712,137 B2 | 4/2014 | Wollenweber |
| 8,745,536 B1 | 6/2014 | Davidson |
| 8,750,450 B2 | 6/2014 | Ulrici et al. |
| 8,803,946 B2 | 8/2014 | Tomita |
| 8,866,883 B2 | 10/2014 | Rohaly et al. |
| 8,885,027 B2 | 11/2014 | Yamaguchi et al. |
| 8,955,978 B2 | 2/2015 | Yanai |
| 8,964,008 B2 | 2/2015 | Bathiche |
| 8,998,417 B2 | 4/2015 | Yanai |
| 9,036,882 B2 | 5/2015 | Masumoto |
| 9,077,982 B2 | 7/2015 | Rha et al. |
| 9,083,963 B2 | 7/2015 | Kamins-Naske et al. |
| 9,094,676 B1 | 7/2015 | Schutten et al. |
| 9,116,666 B2 | 8/2015 | Salter et al. |
| 9,131,913 B2 | 9/2015 | Sehnert et al. |
| 9,142,059 B1 | 9/2015 | Mallet et al. |
| 9,338,445 B2 | 5/2016 | Atkins et al. |
| 9,349,183 B1 * | 5/2016 | Douglas ............... H04N 13/275 |
| 9,473,766 B2 | 10/2016 | Douglas et al. |
| 9,677,741 B2 | 6/2017 | Hsu et al. |
| 9,691,175 B2 | 6/2017 | Rane |
| 9,736,463 B2 | 8/2017 | Gharib et al. |
| 9,769,442 B2 | 9/2017 | Shirai et al. |
| 9,980,691 B2 | 5/2018 | Douglas et al. |
| 9,986,176 B2 | 5/2018 | Moghadam |
| 10,019,812 B2 | 7/2018 | Bendall |
| 10,042,511 B2 | 8/2018 | Roe et al. |
| 10,088,686 B2 | 10/2018 | Robbins et al. |
| 10,136,124 B2 | 11/2018 | MacKenzie et al. |
| 10,297,089 B2 | 5/2019 | Buelow et al. |
| 10,373,309 B2 | 8/2019 | Thiele et al. |
| 10,417,808 B2 | 9/2019 | Noshi et al. |
| 10,492,749 B2 | 12/2019 | Boone et al. |
| 10,545,251 B2 | 1/2020 | Gesbert et al. |
| 10,795,457 B2 | 10/2020 | Douglas et al. |
| 2001/0045979 A1 | 11/2001 | Matsumoto et al. |
| 2002/0068863 A1 | 6/2002 | Slack |
| 2002/0101658 A1 | 8/2002 | Hoppenstein |
| 2002/0105602 A1 | 8/2002 | Pan |
| 2002/0112237 A1 | 8/2002 | Kelts |
| 2002/0113868 A1 | 8/2002 | Park |
| 2002/0183607 A1 | 12/2002 | Bauch et al. |
| 2003/0020809 A1 | 1/2003 | Gibbon et al. |
| 2003/0026474 A1 | 2/2003 | Yano |
| 2003/0107644 A1 | 6/2003 | Choi |
| 2003/0194119 A1 | 10/2003 | Manjeshwar et al. |
| 2003/0204364 A1 | 10/2003 | Goodwin et al. |
| 2003/0218720 A1 | 11/2003 | Morita et al. |
| 2004/0054248 A1 | 3/2004 | Kimchy et al. |
| 2004/0070584 A1 | 4/2004 | Pyo et al. |
| 2004/0082846 A1 | 4/2004 | Johnson et al. |
| 2004/0096799 A1 | 5/2004 | Hughes et al. |
| 2004/0109139 A1 * | 6/2004 | Kiser ............... G02B 27/1053 353/31 |
| 2004/0174605 A1 | 9/2004 | Olsson |
| 2004/0204644 A1 | 10/2004 | Tsougarakis et al. |
| 2004/0208358 A1 | 10/2004 | Tooyama et al. |
| 2004/0223636 A1 | 11/2004 | Edic et al. |
| 2004/0238732 A1 | 12/2004 | State et al. |
| 2004/0246269 A1 | 12/2004 | Serra et al. |
| 2004/0254454 A1 | 12/2004 | Kockro |
| 2005/0017938 A1 | 1/2005 | O'Donnell et al. |
| 2005/0030621 A1 | 2/2005 | Takahashi et al. |
| 2005/0055118 A1 | 3/2005 | Nikolskiy et al. |
| 2005/0062684 A1 | 3/2005 | Geng |
| 2005/0065423 A1 | 3/2005 | Owen |
| 2005/0065424 A1 | 3/2005 | Shah et al. |
| 2005/0096530 A1 | 5/2005 | Daw et al. |
| 2005/0110791 A1 | 5/2005 | Krishnamoorthy et al. |
| 2005/0148848 A1 | 7/2005 | Guang et al. |
| 2005/0151152 A1 | 7/2005 | Miller et al. |
| 2005/0151730 A1 | 7/2005 | Lobregt |
| 2005/0152591 A1 | 7/2005 | Kiraly et al. |
| 2005/0168461 A1 * | 8/2005 | Acosta ............... G06T 15/08 345/419 |
| 2005/0208449 A1 | 9/2005 | Abolfathi et al. |
| 2005/0244050 A1 | 11/2005 | Nomura et al. |
| 2005/0278408 A1 | 12/2005 | Matsumoto |
| 2005/0283063 A1 | 12/2005 | Besson et al. |
| 2005/0285844 A1 | 12/2005 | Morita et al. |
| 2006/0013472 A1 | 1/2006 | Kagitani |
| 2006/0026533 A1 | 2/2006 | Napoli et al. |
| 2006/0033992 A1 | 2/2006 | Solomon |
| 2006/0056680 A1 | 3/2006 | Stutsman et al. |
| 2006/0056726 A1 | 3/2006 | Fujiwara et al. |
| 2006/0058605 A1 | 3/2006 | Deischinger et al. |
| 2006/0077204 A1 | 4/2006 | Pfister et al. |
| 2006/0079755 A1 * | 4/2006 | Stazzone ........... G01R 33/4835 600/410 |
| 2006/0109753 A1 | 5/2006 | Fergason |
| 2006/0120583 A1 | 6/2006 | Dewaele |
| 2006/0171028 A1 | 8/2006 | Oikawa et al. |
| 2006/0173338 A1 | 8/2006 | Ma et al. |
| 2006/0177133 A1 | 8/2006 | Kee |
| 2006/0181482 A1 * | 8/2006 | Iaquinto ............... A61B 90/36 345/8 |
| 2006/0210111 A1 | 9/2006 | Cleveland et al. |
| 2006/0210147 A1 | 9/2006 | Sakaguchi |
| 2006/0227103 A1 | 10/2006 | Koo et al. |
| 2006/0232665 A1 | 10/2006 | Schowengerdt et al. |
| 2006/0238441 A1 | 10/2006 | Benjamin et al. |
| 2006/0239523 A1 | 10/2006 | Stewart et al. |
| 2006/0241458 A1 * | 10/2006 | Hayashi ............... A61B 8/06 600/453 |
| 2006/0268104 A1 | 11/2006 | Cowan et al. |
| 2006/0279569 A1 | 12/2006 | Acosta et al. |
| 2006/0286501 A1 | 12/2006 | Chishti et al. |
| 2007/0021738 A1 | 1/2007 | Hasser et al. |
| 2007/0035830 A1 | 2/2007 | Matveev et al. |
| 2007/0040854 A1 | 2/2007 | Lievin et al. |
| 2007/0053562 A1 | 3/2007 | Reinhardt et al. |
| 2007/0058249 A1 | 3/2007 | Hirose et al. |
| 2007/0085902 A1 | 4/2007 | Walker et al. |
| 2007/0103459 A1 | 5/2007 | Stoval, III et al. |
| 2007/0116357 A1 | 5/2007 | Dewaele |
| 2007/0118408 A1 | 5/2007 | Mahesh et al. |
| 2007/9115204 | 5/2007 | Budz et al. |
| 2007/0146325 A1 | 6/2007 | Poston et al. |
| 2007/0147671 A1 | 6/2007 | Di Vincenzo et al. |
| 2007/0165927 A1 | 7/2007 | Muradyan et al. |
| 2007/0167801 A1 | 7/2007 | Webler et al. |
| 2007/0188520 A1 | 8/2007 | Finley et al. |
| 2007/0206155 A1 | 9/2007 | Lipton |
| 2007/0237369 A1 | 10/2007 | Brunner et al. |
| 2007/0263915 A1 * | 11/2007 | Mashiach ........... G06K 9/4638 382/130 |
| 2007/0274585 A1 | 11/2007 | Zhang et al. |
| 2007/0279435 A1 | 12/2007 | Ng et al. |
| 2007/0279436 A1 | 12/2007 | Ng et al. |
| 2007/0285774 A1 | 12/2007 | Merrir et al. |
| 2008/0025584 A1 | 1/2008 | Kunz |
| 2008/0033240 A1 | 2/2008 | Hoffman et al. |
| 2008/0037843 A1 | 2/2008 | Fu et al. |

(56) References Cited

U.S. PATENT DOCUMENTS

| | | |
|---|---|---|
| 2008/0044069 A1 | 2/2008 | DuGal |
| 2008/0055305 A1 | 3/2008 | Blank et al. |
| 2008/0055310 A1 | 3/2008 | Mitchell et al. |
| 2008/0062173 A1 | 3/2008 | Tashiro |
| 2008/0088621 A1 | 4/2008 | Grimaud et al. |
| 2008/0094398 A1 | 4/2008 | Ng et al. |
| 2008/0100612 A1 | 5/2008 | Dastmalchi et al. |
| 2008/0117233 A1 | 5/2008 | Mather et al. |
| 2008/0154952 A1 | 6/2008 | Waldinger et al. |
| 2008/0267499 A1 | 10/2008 | Deischinger et al. |
| 2008/0267527 A1 | 10/2008 | Berretty |
| 2008/0281182 A1 | 11/2008 | Rabben et al. |
| 2008/0291268 A1 | 11/2008 | Berretty |
| 2008/0297434 A1 | 12/2008 | Abileah |
| 2009/0016491 A1 | 1/2009 | Li |
| 2009/0034684 A1 | 2/2009 | Bernard et al. |
| 2009/0040227 A1 | 2/2009 | Vrba |
| 2009/0051685 A1 | 2/2009 | Takagi et al. |
| 2009/0080765 A1 | 3/2009 | Bernard et al. |
| 2009/0119609 A1 | 5/2009 | Matsumoto |
| 2009/0147073 A1 | 6/2009 | Getty |
| 2009/0217209 A1 | 8/2009 | Chen et al. |
| 2009/0219283 A1 | 9/2009 | Hendrickson et al. |
| 2009/0219383 A1 | 9/2009 | Passmore |
| 2009/0231697 A1 | 9/2009 | Marcus et al. |
| 2009/0232275 A1 | 9/2009 | Spartiotis et al. |
| 2009/0237492 A1 | 9/2009 | Kikinis et al. |
| 2009/0244267 A1 | 10/2009 | Yuan et al. |
| 2009/0278917 A1 | 11/2009 | Dobbins et al. |
| 2009/0282429 A1 | 11/2009 | Olsson et al. |
| 2009/0304232 A1 | 12/2009 | Tsukizawa |
| 2009/0324052 A1 | 12/2009 | Nowinski |
| 2010/0045783 A1 | 2/2010 | State et al. |
| 2010/0081912 A1 * | 4/2010 | McKenna ........... A61B 5/02007 600/368 |
| 2010/0085423 A1 | 8/2010 | Lange |
| 2010/0194861 A1 | 8/2010 | Hoppenstein |
| 2010/0201785 A1 | 8/2010 | Lantin |
| 2010/0231705 A1 | 9/2010 | Yahav et al. |
| 2010/0246911 A1 | 9/2010 | Rabben et al. |
| 2011/0026808 A1 | 2/2011 | Kim et al. |
| 2011/0043644 A1 | 2/2011 | Munger et al. |
| 2011/0063576 A1 | 3/2011 | Redmann et al. |
| 2011/0107270 A1 | 5/2011 | Wang et al. |
| 2011/0109620 A1 | 5/2011 | Hong et al. |
| 2011/0141246 A1 | 6/2011 | Schwartz et al. |
| 2011/0194728 A1 | 8/2011 | Kutcka et al. |
| 2011/0196237 A1 * | 8/2011 | Pelissier ................. A61B 8/467 600/454 |
| 2011/0228051 A1 | 9/2011 | Dedoglu et al. |
| 2011/0254845 A1 | 10/2011 | Oikawa et al. |
| 2011/0273543 A1 | 11/2011 | Ushio et al. |
| 2011/0279450 A1 | 11/2011 | Seong et al. |
| 2012/0008734 A1 | 1/2012 | Thomson et al. |
| 2012/0008735 A1 | 1/2012 | Maurer et al. |
| 2012/0013711 A1 | 1/2012 | Tamir et al. |
| 2012/0019636 A1 | 1/2012 | Gefen et al. |
| 2012/0038631 A1 | 2/2012 | Mayhew et al. |
| 2012/0056998 A1 | 3/2012 | Kang et al. |
| 2012/0071755 A1 | 3/2012 | Zheng et al. |
| 2012/0075293 A1 | 3/2012 | Kuwabara et al. |
| 2012/0113235 A1 | 5/2012 | Shintani |
| 2012/0120202 A1 | 5/2012 | Yoon et al. |
| 2012/0120207 A1 | 5/2012 | Shimazaki et al. |
| 2012/0127284 A1 | 5/2012 | Bar-Zeev et al. |
| 2012/0162219 A1 | 6/2012 | Kobayashi et al. |
| 2012/0190439 A1 | 7/2012 | Nourbakhsh |
| 2012/0190967 A1 | 7/2012 | Nahm |
| 2012/0202665 A1 | 8/2012 | Sakai et al. |
| 2012/0209106 A1 | 8/2012 | Liang et al. |
| 2012/0215218 A1 | 8/2012 | Lipani |
| 2012/0224755 A1 | 9/2012 | Wu |
| 2012/0229595 A1 | 9/2012 | Miller |
| 2012/0242569 A1 | 9/2012 | Hamagishi |
| 2012/0269424 A1 | 10/2012 | Ebata et al. |
| 2012/0287361 A1 | 11/2012 | Sugihara |
| 2012/0306849 A1 | 12/2012 | Steen |
| 2013/0002646 A1 | 1/2013 | Lin et al. |
| 2013/0003020 A1 | 1/2013 | Koehler et al. |
| 2013/0057830 A1 | 3/2013 | Tsai et al. |
| 2013/0070984 A1 | 3/2013 | Shirasaka et al. |
| 2013/0141552 A1 | 6/2013 | Kwon |
| 2013/0176566 A1 | 7/2013 | Mitchell et al. |
| 2013/0182085 A1 | 7/2013 | Ziarati |
| 2013/0242063 A1 | 9/2013 | Matsumoto |
| 2013/0245375 A1 | 9/2013 | DiMaio et al. |
| 2013/0251242 A1 | 9/2013 | Suzuki et al. |
| 2013/0278727 A1 | 10/2013 | Tamir et al. |
| 2013/0335417 A1 | 12/2013 | McQueston et al. |
| 2014/0051988 A1 | 2/2014 | Lautenschlager |
| 2014/0063376 A1 | 3/2014 | Tsang et al. |
| 2014/0065663 A1 | 3/2014 | Vasquez et al. |
| 2014/0176685 A1 | 6/2014 | Oikawa et al. |
| 2014/0210965 A1 | 7/2014 | Goodman et al. |
| 2014/0253698 A1 | 9/2014 | Evans et al. |
| 2014/0253699 A1 | 9/2014 | Schafer et al. |
| 2014/0307067 A1 * | 10/2014 | Douglas ............... H04N 13/344 348/53 |
| 2014/0340400 A1 | 11/2014 | Takeguchi et al. |
| 2014/0347726 A1 | 11/2014 | Yang et al. |
| 2015/0077713 A1 | 3/2015 | Drumm |
| 2015/0379351 A1 * | 12/2015 | Dibenedetto ....... H04N 5/44504 345/633 |
| 2016/0038248 A1 | 2/2016 | Bharadwaj et al. |
| 2016/0287201 A1 | 10/2016 | Bergtholdt et al. |
| 2016/0302895 A1 | 10/2016 | Rohaly et al. |
| 2018/0116728 A1 * | 5/2018 | Lang ..................... A61B 90/36 |
| 2018/0168740 A1 * | 6/2018 | Ryan ...................... A61B 34/25 |

FOREIGN PATENT DOCUMENTS

| | | | |
|---|---|---|---|
| DE | 19534750 A1 | 3/1997 | |
| DE | 102011080588 A1 | 2/2013 | |
| EP | 0571827 A | 12/1993 | |
| EP | 0592652 B1 | 9/1997 | |
| EP | 0918242 A1 | 5/1999 | |
| EP | 1056049 A2 | 11/2000 | |
| EP | 1056049 A2 * | 11/2000 | ........... H04N 13/383 |
| EP | 0970589 B1 | 8/2004 | |
| EP | 1683485 A1 | 7/2006 | |
| EP | 1791087 A | 5/2007 | |
| EP | 1843296 A1 | 10/2007 | |
| FR | 2838598 B1 | 10/2004 | |
| JP | H 09-205660 | 8/1997 | |
| JP | H 11-232010 A | 8/1999 | |
| JP | 2000-333950 A | 12/2000 | |
| JP | 2001-504603 A | 4/2001 | |
| JP | 2002-330958 A | 11/2002 | |
| JP | 2005-130309 A | 5/2005 | |
| JP | 2005-521960 A | 7/2005 | |
| JP | 2006-113088 A | 4/2006 | |
| JP | 3816599 B2 | 6/2006 | |
| JP | 2008-220406 A | 9/2008 | |
| JP | 2009-000167 A | 1/2009 | |
| JP | 2009-018048 A | 1/2009 | |
| JP | 2009-022476 A | 2/2009 | |
| JP | 2009-515404 A | 4/2009 | |
| JP | 4319165 B2 | 6/2009 | |
| JP | 4519898 B2 | 5/2010 | |
| JP | 2012-105796 A | 6/2012 | |
| JP | 2012-142846 A | 7/2012 | |
| JP | 2013-538360 A | 10/2013 | |
| JP | 2014-222459 A | 11/2014 | |
| JP | 2015-036084 A | 2/2015 | |
| KR | 10-2004-0076846 A | 9/2004 | |
| KR | 10-2006-0085596 A | 7/2006 | |
| KR | 10-0659327 B1 | 12/2006 | |
| KR | 10-2007-0082138 A | 8/2007 | |
| KR | 10-2011-0125416 A | 11/2011 | |
| KR | 10-1083808 B1 | 11/2011 | |
| KR | 19-2012-0051065 A | 5/2012 | |
| KR | 10-1162053 B1 | 7/2012 | |
| KR | 10-2014-0048994 A | 4/2014 | |
| WO | WO 95/00872 | 1/1995 | |

(56) References Cited

FOREIGN PATENT DOCUMENTS

| WO | WO 97/00482 | 1/1997 |
|---|---|---|
| WO | WO 97/46029 | 12/1997 |
| WO | WO 99/23586 | 5/1999 |
| WO | WO 01/005161 | 1/2001 |
| WO | WO 03/010977 | 2/2003 |
| WO | WO 03/083781 | 10/2003 |
| WO | WO 03/100542 | 12/2003 |
| WO | WO 2005/062629 | 7/2005 |
| WO | WO 2006/038744 | 4/2006 |
| WO | WO 2007/052216 | 5/2007 |
| WO | WO 2007/059477 | 5/2007 |
| WO | WO 2007/063442 | 6/2007 |
| WO | WO 2009/076303 | 6/2009 |
| WO | WO 2011/031315 | 3/2011 |
| WO | WO 2011/160200 | 12/2011 |
| WO | WO 2012/030091 | 3/2012 |
| WO | WO 2012/101395 | 8/2012 |
| WO | WO 2012/144453 | 10/2012 |
| WO | WO 2013/01 1035 | 1/2013 |
| WO | WO 2015/069049 | 5/2015 |

OTHER PUBLICATIONS

Notice of Allowance for U.S. Appl. No. 17/095,411 dated Feb. 2, 2021.
Documents filed with U.S. District Court Proceedings for *D3D Technologies, Snc.* v. *Microsoft Corporation*; U.S. District Court, Middle District of Florida Orlando Division; Civil Action No. 6:2Q-cv-01699-GAP-DCI; Includes publicly available documents filed from Nov. 9, 2020-Jan. 4, 2021; Docket Nos. 22-41; (1,536 pages).
Documents filed with U.S. District Court Proceedings for *D3D Technologies, Inc.* v. *Microsoft Corporation*; U.S. District Court, Middle District of Florida Orlando Division; Civil Action No. 6:20-cv-01699-GAP-DCI; Includes publicly available documents filed from Jan. 6, 2021-Feb. 3, 2021; Docket Nos. 42-46; (96 pages).
Inter Partes Review—*Microsoft Corporation* v. *D3D Technologies, Inc*; United States Patent and Trademark Office—Before the Patent Trial and Appeal Board, Case No. IPR2021-00703.
Foley et al. "The Systems Programming Series: Computer Graphics: Principles and Practice Second Edition" Addison-Wesley Publishing Company; 1990.
Documents filed with U.S. District Court Proceedings for *D3D Technologies, Inc.* v. *Microsoft Corporation*; U.S. District Court, Middle District of Florida Orlando Division; Civil Action No. 6:20-cv-01699-GAP-DCI; includes publicly available documents filed from Feb. 4, 2021-Apr. 6, 2021; Docket Nos. 47-69; (1,242 pages).
Petition for Inter Partes Review of U.S. Pat. No. 9,473,766, including Exhibits 1001-1024; Case No. IPR2021-00703, filed Apr. 7, 2021 (1,441 pages).
U.S. Appl. No. 11/941,578, filed Nov. 16, 2007 U.S. Pat. No. 8,384,771.
U.S. Appl. No. 12/176,569, filed Jul. 21, 2008 U.S. Pat. No. 9,349,183.
U.S. Appl. No. 14/313,398, filed Jun. 24, 2014 U.S. Pat. No. 9,473,766.
U.S. Appl. No. 14/877,442 filed Oct. 7, 2015 U.S. Pat. No. 9,980,691.
U.S. Appl. No. 15/878,463 filed Jan, 24, 2018 U.S Pat. No, 10,795,457.
*D3D Technologies, Inc.* v. *Microsoft Corporation*. U.S. District Court, Middle District of Florida Orlando Division; Civil Action No. 6:20-cv-01 699-GAP-DCI.
U.S. Appl. No. 17/021,548, filed Sep. 15, 2020, Douglas et al..
U.S. Appl. No. 17/095,411, filed Nov. 11, 2020, Douglas et al..
U.S. Appl. No. 17/122,549, filed Dec. 15, 2020, Douglas et al..
U.S. Appl. No. 60/842,377, filed Sep. 6, 2006, Nowinski.
U.S. Appl. No. 60/854,872, filed Oct. 27, 2006, Dastmalchi et al..
Bakalash, Reuven et al. "Medicube: A 3D Medical Imaging Architecture" Computer &Graphics vol. 13, No. 2, pp. 151-157; 1989.
Douglas, David B. et al. "Augmented Reality Imaging System: 3D Viewing of a Breast Cancer" J Nat Sci, 2016;2(9).
Douglas, David B. et al. "Augmented Reality: Advances in Diagnostic Imaging: Multimodal Technologies and Interaction" 2017;1(4):29.
Douglas, David B. et al. "D3D Augmented Reality Imaging System: Proof of Concept in Mammography" Med Devices (Auckl), 2016; 9:277-83.
Engel, K., et al. "Combining Local and Remote Visualization Techniques for Interactive Volume Rendering in Medical Applications" Proceedings Visualization 2000. VIS 2000 (Cat. No. 00CH37145), Salt Lake City, UT, USA, 2000, pp. 449-452.
Erickson, Bradley J. "A Desktop Computer-Based Workstation for Display and Analysis of 3-and 4-Dimensional Biomedical Images" Computer Methods and Programs in Biomedicine, 30; pp. 97-110; 1989.
Goodsitt, Mitchel M. et al "Stereomammography: Evaluation of Depth Perception using a Virtual 3D Cursor" Med. Phys. 27 (6), Jun. 2000.
Haker, Steven et al. "Nondistorting Flattening Maps and the 3-D Visualization of Colon CT Images" IEEE Transactions of Medical Imaging; vol. 19, No. 7; Jul. 2000; 665-670.
Hinckley, Ken "Haptic Issues forVirtual Manipulation" A Dissertation Presented to the Faculty of the School of Engineering and Applied Science at the University of Virginia; Dec. 1996.
Hinckley, Ken, et al. "New Applications for the Touchscreen in 2D and 3D Medical Imaging Workstations" Proc. SPIE Medical Imaging '95: Image Display, SPIE vol. 2431, pp. 110-118.
Hui, Y.W. et al "3D Cursors for Volume Rendering Applications" EEE Conference on Nuclear Science Symposium and Medical Imaging, Orlando, FL, USA, 1992, pp. 1243-1245 vol. 2.
Hong, Lichan et al. "Reconstruction and Visualization of 3D Models of Colonic Surface" IEEE Transactions on Nuclear Science, vol. 44, No. 3, Jun. 1997.
IBM "Fast Inspection of Contents of a Volume of 3D Data" IBM Technical Disclosure Bulletin; Feb. 1, 1994; vol. 37, Issue 2A.
Interrante, Victoria et al. "Strategies for Effectively Visualizing 3D Flow with Volume LIC" IEEE Visualization Conference; 1997; pp. 1-4.
Kapur, Ajay et al. "Combination of Digital Mammography with Semi-Automated 3D Breast Ultrasound" NIH Public Access; Author Manuscript; Technol Cancer Res Treat, 3(4): 325-334; Aug. 2004.
Kaufman, A., et a. "Real-Time Volume Rendering" International Journal of Imaging Systems and Technology, special issue on 3D: 2000.
Klein, GJ et al. "A 3D Navigational Environment for Specifiying Positron Emission Tomography Volumes-of-Interest" 1995 IEEE Nuclear Science Symposium and Medical Imaging Conference Record, San Francisco, CA, USA, 1995, pp. 1452-1455 vol. 3.
Kok, Arjan J.F. et al. "A Multimodal Virtual Reality Interface for 3D Interaction with VTK" Knowledge and Information Systems; 2007.
Kreeger, Kevin et al. "Interactive Volume Segmentation with the PAVLOV Architecture" Proceedings 1999 IEEE Parallel Visualization and Graphics Symposium (Cat. No. 99EX381), San Francisco, CA, USA, 1999, pp. 61-119.
Li, Yanhong et al. "Tinkerbell—A Tool for Interactive Segmentation of 3D Data" Journal of Structural Biology 120, 266-275; 1997.
Löbbert, Sebastian et al. "Visualisation of Two-Dimensional Volumes" 2004.
Loh, Yong Chong et al. "Surgical Planning System with Real-Time Volume Rendering" Proceedings International Workshop on Medical Imaging and Augmented Reality, Shatin, Hong Kong, China, 2001 , pp. 259-261.
Martin, RW et al. "Stereographic Viewing of 3D Ultrasound Images: A Novelty or a Tool?" 1995 IEEE Ulstrasonics Symposium; IEEE Press 1431-1434.
Peterson, Christine M. et al. "Volvulus of the Gastrointesinal Tract: Appearances at Multi-Modality Imaging" Radiographics; vol. 29, No. 5; Sep.-Oct. 2009; pp. 1281-1293.
Piekarski, Wayne "Interactive 3D Modelling in Outdoor Augmented Reality Worlds" Wearable Computer Lab, School of Computer and Information Science; The University of South Australia; Feb. 2004.

(56) References Cited

OTHER PUBLICATIONS

Robb, R. A., et al. "A Workstation for Interactive Display and Quantitative Analysis of 3-D and 4-D Biomedical Images" Biodynamics Research Unit, IEEE, 1986.
Robb, R.A. et al. "Interactive Display and Analysis of 3-D Medical Images" IEEE Transactions on Medical Imaging, vol. 8, No. 3, Sep. 1989.
Skoglund, T. et al. "3D Reconstruction of Biological Objects from Sequential Image Planes—Applied on Cerebral Cortex for CAT" Computerized Medical Imaging and Graphics; vol. 17, No. 3, pp. 165-174; 1993.
Steinicke, Frank et al. "Towards Applicable 3D User Interfaces for Everyday Working Environments" Conference Paper; Sep. 2007.
Subramanian, Sriram "Tangible Interfaces for Volume Navigation" CIP-Data Library Technische University Eindhoven; 2004.
Vanacken, Lode et al. "Exploring the Effects of Environment Density and Target Visibility on Object Selection in 3D Virtual Environments" IEEE Symposium on 3D User Interfaces 2007, Mar. 10-11.
Ware, Colin et al. "Selection Using a One-Eyed Cursor in a Fish Tank VR Environment" Faculty of Computer Science, University of new Brunswick; Apr. 20, 2000.
Wither, Jason et al. "Pictorial Depth Cues for Outdoor Augmented Reality" Ninth IEEE International Symposium on Wearable Computers (ISWC'05), Osaka, 2005, pp. 92-99.
Wong, Terence Z. et al. "Stereoscopically Guided Characterization of Three-Dimensional Dynamic MR Images of the Breast" Radiology, 1996; 198:288-291.
Yushkevich, Paul A et al. "User-Guided 3D Active Contour Segmentation of Anatomical Structures: Significantly Improved Efficiency and Reliability" NeuroImage 31; 1116-1128; 2006.
Zhai, Shurnin et al. "The Partial Occlusion Effect: Utilizing Semi-Transparency in 3D Human Computer Interaction" ACM Transactions on Computer-Human Interaction, 3(3), 254-284; 1996.
Office Action for U.S. Appl. No. 11/941,578, dated Sep. 29, 2011.
Office Action for U.S. Appl. No. 11/941,578, dated Feb. 22, 2012.
Notice of Allowance for U.S. Appl. No. 11/941,578, dated Dec. 21, 2012.
Office Action for U.S. Appl. No. 12/176,569, dated Apr. 4, 2012.
Office Action for U.S. Appl. No. 12/176,569, dated Oct. 26, 2012.
Office Action for U.S. Appl. No. 12/176,569, dated Jul. 15, 2014.
Office Action for U.S. Appl. No. 12/176,569, dated Feb. 5, 2015.
Notice of Allowance for U.S. Appl. No. 12/176,569, dated May 29, 2015.
Office Action for U.S. Appl. No. 14/313,398 dated Sep. 25, 2015.
Office Action for U.S. Appl. No. 14/313,398 dated May 12, 2016.
Notice of Allowance for U.S. Appl. No. 14/313,398 dated Jul. 15, 2016.
Office Action for U.S. Appl. No. 14/877,442 dated Jul. 14, 2017.
Office Action for U.S. Appl. No. 14/877,442 dated Dec. 5, 2017.
Notice of Allowance for U.S. Appl. No. 14/877,442 dated Apr. 5, 2018.
Office Action for U.S. Appl. No. 15/878,463 dated Jun. 13, 2019.
Office Action for U.S. Appl. No. 15/878,463 dated Sep. 24, 2019.
Office Action for U.S. Appl. No. 15/878,463 dated Feb. 24, 2020.
Notice of Allowance for U.S. Appl. No. 15/878,463 dated Aug. 10, 2020.
Documents filed with U.S. District Court Proceedings for *D3D Technologies, Inc. v. Microsoft Corporation*; U.S. District Court, Middle District of Florida Orlando Division; Civil Action No. 6:20-cv-01699-GAP-DCI; Includes publicly available documents filed from Sep. 16, 2020-Oct. 6, 2020; (991 pages).
Moreira, Dilvan A. et al. "3D Markup of Radiological Images in ePAD, a Web-Based Image Annotation Tool" 2015 IEEE 28th International Symposium on Computer-Based Medical Systems; 2015.
Documents filed with U.S. District Court Proceedings for *D3D Technologies, Inc. v. Microsoft Corporation*; U.S. District Court, Middle District of Florida Orlando Division; Civil Action No. 6:20-cv-01699-GAP-DCI; Includes publicly available documents filed on Apr. 19, 2021; Docket No. 70; (76 pages).
Defendant Microsoft Corporation's Supplemental Invalidity Contentions for *D3D Technologies, Inc. v. Microsoft Corporation*; U.S. District Court, Middle District of Florida Orlando Division; Civil Action No. 6:20-cv-01699-GAP-DCI; Filed Apr. 19, 2021 (143 pages).
Documents filed with *Microsoft Corporation v. D3D Technologies, Inc.*; United States Patent and Trademark Office—Before the Patent Trial and Appeal Board, Case No. IPR2021-00647; Filed on Apr. 15, 2021 (8 pages).
Documents filed with *Microsoft Corporation v. D3D Technologies, Inc.*; United States Patent and Trademark Office—Before the Patent Trial and Appeal Board, Case No. IPR2021-00643; filed Apr. 15, 2021 (8 pages).
Documents filed with *Microsoft Corporation v. D3D Technologies, Inc.*; United States Patent and Trademark Office—Before the Patent Trial and Appeal Board, Case No. IPR2021-00703; Filed on Apr. 15, 2021 (14 pages).
U.S. Appl. No. 60/673,257, filed Apr. 20, 2005, Bar-Zohar et al..
U.S. Appl. No. 60/835,852, filed Aug. 4, 2006, Anderson et al..
Azuma, Ronald T. "A Survey of Augmented Reality" In Presence: Teleoperators and Virtual Environments 6, 4 (Aug. 1997) pp. 355-385.
By the Editors of Electronic Gaming Monthly "1993 Video Game Preview Guide" 1993.
Cakmakci, Ozan et al. "Head-Worn Displays: A Review" Journal of Display Technology, vol. 2, No. 3, Sep. 2006.
Calhoun, Paul S. et al. "Three-Dimensional Volume Rendering of Spiral CT Data: Theory and Method" Radio Graphics; vol. 19, No. 3; May-Jun. 1999.
CBRStaffWriter "Sense8 Launches World Up, Virtual Reality Tool" CBR; https://www.cbronline.com; Sep. 8, 1995.
Cochrane, Nathan "VFX-1 Virtual Reality Helmet by Forte" Game Bytes Magazine; 1994.
D'Orazio, Dante et al. "Valve's VR Headset is Called the Vive and it's Made by HTC" The Verge; https://www.theverge/com/2015/3/1/8127445/htc-vive-valve-vr-headset Mar. 1, 2015.
Digest of Papers "First International Symposium on Wearable Computers" IEEE Computer Society Technical Committee on Fault Tolerant Computing; Cambridge, MA; Oct. 13-14, 1997 (5 pages).
Digest of Papers "Second International Symposium on Wearable Computers" IEEE Computer Society Technical Committee on Fault Tolerant Computing; Pittsburgh, PA; Oct. 19-20, 1998 (6 pages).
Doneus, Michael et al. "Anaglyph Images—Still A Good Way to Look at 3D-Objects?" Oct. 1999.
Edirisinghe, E.A. et al. "Stereo imaging, An Emerging Technology" Jan. 2000.
Fisher, Scott S. "Portfolio of Work: Environmental Media Project" Graduate School of Media and Governance, Keio University, Tokyo, Japan 1999—Current.
Fisher, Scott S. "Portfolio of Work: Menagerie" Telepresence Research, Inc. San Francisco, CA 1993.
Fisher, Scott S. "Portfolio of Work: NASA VIEWlab" NASA Ames Research Center, Mountain View CA 1985-90.
Fisher, Scott S. "Portfolio of Work: Stereoscopic Workstation" Architecture Machine Group, MIT, Cambridge, MA 1981.
Fisher, Scott S. "Portfolio of Work: Telepresence Mobile Robot" Telepresence Research, Inc., San Francisco, CA 1991.
Fisher, Scott S. "Portfolio of Work: Viewpoint Dependent Imaging" Architecture Machine Group, MIT, Cambridge, MA 1981.
Fisher, Scott S. Portfolio of Work: Virtual Brewery Adventure: Telepresence Research, Inc., San Francisco, CA 1994.
Fisher, Scott S. "Portfolio of Work: Virtual Explorer" University of California, San Diego, CA 1998.
Fisher, Scott S. et al. "Virtual Interface Environment Workstations" Proceedings of the Human Factors Society—32nd Annual Meeting—1988.
Fisher, Scott S. "Portfolio of Work; VRML Projects" Telepresence Research, Inc., San Francisco, CA 1996.
Fuhrmann, A.L. et al. "Distributed Software-Based Volume Visualization in a Virtual Environment" The Eurographics Association and Blackwell Publishing; vol. 0, No. 0, pp. 1-11; 1981.

(56) References Cited

OTHER PUBLICATIONS

Galton, N. "Fast Inspection of Contents of a Volume of 3D Data" IBM Technical Disclosure Bulletin; ip.com; Feb. 1, 1994 (3 pages).
He, Changming "Volume Visualization in Projection-Based Virtual Environments; Interaction and Exploration Tools Design and Evaluation" Griffith University; 2011.
Heuser, John E. "Membrane Traffic in Anaglyph Stereo" Munksgaard International Publishers; Traffic 2000, vol. 1, 35-37.
IEEE 1998 Virtual Reality Annual International Symposium IEEE Computer Society; Atlanta, GA; Mar. 14-18, 1998 (8 pages).
Interrante, Victoria et al. "Strategies for Effectively Visualizing 3D Flow with Volume LIC" IEEE Visualization Conference; 1997; pp. 1-5.
Kaluszka, Aaron "3DS North American Price, Date, Colors Set" NintendoWorld Report; Jan. 19, 2011.
Kancherla, Anantha R. et al. "A Novel Virtual Reality Tool for Teaching Dynamic 3D Anatomy" Conference Paper; Jan. 1995.
Kato, Hirokazu et al, "Marker Tracking and HMD Calibration for a Video-Based Augmented Reality Conferencing System" IWAR '99: Proceedings of the 2nd IEEE and ACM International Workshop on Augmented Reality; Oct. 1999.
Kniss, Joe et al. "Interactive Texture-Based Volume Rendering for Large Data Sets" IEEE Computer Graphics and Applications; Jul./Aug. 2001.
Krapichler, Christian et al. "VR Interaction Techniques for Medical Imaging Applications" Computer Methods and Programs in Biomedicine 56; pp. 65-74; 1998.
Kratz, Andrea et al. "GPU-Based High-Quality Volume Rendering for Virtual Environments" Oct. 2006.
Kratz, Andrea "Integration of Hardware Volume Renderer into a Virtual Reality Application" Universitat Koblenz Landau; Oct. 2005.
Kress, Bernard et al. "Speckle Reduction Technique for Laser Based Automotive Head Up Display (HUD) Projectors" Proceedings vol. 8026, Photonic Applications for Aerospace, Transportation, and Harsh Environment II; 80260P (2011) https://doi.org/10.1117/12.886536; May 26, 2011.
Lima, Luis Alberto et al. "Virtual Seismic Interpretation" IEEE XI SIBGRAPI Proceedings, Oct. 1998.
Lorensen, Wifiiarn E. et al. "Marching Cubes: A High Resolution 3D Surface Construction Algorithm" Siggraph '87: Proceedings of the 14th annual conference on Computer graphics and interactive techniques Aug. 1987.
Marescaux, Jacques et al. "Augmented-Reality-Assisted Laparoscopic Adrenalectomy" Journal of American Medical Association; vol. 292, No. 18; Nov. 10, 2004.
McAllister, David F. "Display Technology: Stereo & 3D Display Technologies" Mar. 2003.
McKenna, Michael et al. "Three Dimensional Visual Display Systems for Virtual Environments" The Massachusetts Institute of Technology; Presence, vol. 1, No. 4, Fall 1992.
Mellott "Cybermaxx Virtual Reality Helmet" Mellott's VR; https://www.mellottsvrpage.com/index/php/cybermaxx-virtual-reality-helmet/; Jan. 26, 2021.
Moeller, D.P.F "Mathematical and Computational Modeling and Simulation: Fundamentals and Case Studies" Springer-Verlag Berlin Heidelber; 2004.
NASA "The Virtual Interface Environment Workstation (VIEW)" Partnership with VPL Research, Inc.; https://www.nasa.gov/ames/spinoff/new_continent_of_ideas/; 1990.
Osorio, Angel et al. "A New PC Based on Software to Take and Validate Clinical Decisions for Colorectal Cancer using Metric 3D Images Segmentations" https://dx.doi.org/10.1594/ecr2010/C-1071; 10.1594/ecr2010/C-1071; 2010.
PlayStation "Announcing the Price and Release Date for PlayStation VR" Available at https://www.youtube.corn/watch?v=wZ57C13Nq6o; Mar. 15, 2016.
Popescu, Voicu et al. "Three-Dimensional Display Rendering Acceleration Using Occlusion Camera Reference Images" Journal of Display Technology, vol. 2, No. 3, Sep. 2006.
Radeva, Nadezhda et al. "Generalized Temporal Focus+Context Framework for Improved Medical Data Exploration" Society for Imaging Informatics in Medicine; Jan. 8, 2014.
Rosenberg, Adam "Hands-On with Oculus Rift, John Carmack's Virtual Reality Goggles" G4 Media, LLC; Jun. 14, 2012.
Schmalstieg, Dieter et al "The Studierstube Augmented Reality Project" https://arbook.icg.tugraz.at/schmalstieg/Schmalstieg_045.pdf; 2005.
ScienceDaily "FDA Approves New Robotic Surgery Device" ScienceDaily; Food and Drug Administration; Jul. 17, 2000.
Soler, L., et al. "Virtual Reality and Augmented Reality in Digestive Surgery" Proceedings of the Third IEEE and ACM International Symposium on Mixed and Augmented Reality; 2004.
Soler, Luc et al. "Virtual Reality, Augmented Reality, and Robotics Applied to Digestive Operative Procedures: From in Vivo Animal Preclinical Studies to Clinical use" Proceedings of SPIE; 2006.
Sony "Sony Global—Product & Technology Milestones—Projector" https://www.sony.net/SonyInfo/Corporateinfo/History/sonyhistory-n.html; printed Feb. 23, 2021.
Sony "Projector Head Mounted Display" Sony Global—Product & Technology Milestones-Projector Head Mounted Display; https://www.sony.net/SonyInfo/Corporateinfo/History/sonyhistory-n.html; Jan. 26, 2021.
Storey, Neil et al. "Interactive Stereoscopic Computer Graphic Display Systems" Proc. Ineract '84; pp. 163-168; Sep. 4-7, 1984.
Sutherland, Ivan E. "A Head-Mounted Three Dimensional Display" Fall Join Computer Conference, 1968.
The Computer Chronicles "Virtual Reality" available at https://www.youtube.com/watch?v=wfHMSqQKg6s; 1992.
Tresens, Marc Antonijuan et al. "Hybrid-Reality: A Collaborative Environment for Biomedial Data Exploration Exploiting 2-D and 3-D Correspondence" Studies in Health Technology and Informatics; Feb. 2004.
Ultrasound Visualization Research "UNC Ultrasound/Medical Augmented Reality Research: Augmented Reality Technology" https://www.cs.unc,edu/Research/us/; Jun. 15, 2000.
Vidal, F. P. et al. "Principles and Applications of Medical Virtual Environments" Eurographics 2004.
V-Rtifacts "Retrospective Photo Review of Forte VFX1 Virtual Reality System" https://wwvrtifacts.com/retrospective-photo-review-of-forte-vfx1-virtual-reality-system/; Jan. 26, 2021.
V-Rtifacts "Teardown—Virtual Research V6: Head Mounted Displays, How-To; Teardowns; Tutorials, Stereoscopic 3D, VR Companies" https://vrtifacts.com/teardown-virtual-research-v6/; printed Jan. 26, 2021.
Wikipedia "MechWarrior 2: 31st Century Combat" https://en.wikipedia.org/wiki/MechWarrior_2:_31st_Century_Combat; Jan. 26, 2021.
Wikipedia "Virtual Boy" https://en.wikipedia.org/wiki/Virtual_Boy; Jan. 11, 2021.
Wikipedia "VPL Research" https://en.wikipedia.org/wiki/VPL_Research; Jan. 22, 2021.
Notice of Allowance for U.S. Appl. No. 17/122,549 dated Mar. 3, 2021.
Defendant Microsoft Corporation's Preliminary Noninfringement Contentions for *D3D Technologies, Inc.* v. *Microsoft Corporation*; U.S. District Court, Middle District of Florida Orlando Division; Civil Action No. 6:20-cv-01699-GAP-DCI Filed Feb. 4, 2021 (1,114 Pages).
Inter Partes Review—*Microsoft Corporation* v. *D3D Technologies, Inc*; United States Patent and Trademark Office—Before the Patent Trial and Appeal Board, Case No. IPR2021-00647.
Inter Partes Review—*Microsoft Corporation* v. *D3D Technologies, Inc*; United States Patent and Trademark Office—Before the Patent Trial and Appeal Board, Case No. IPR2021-00648.
U.S. Appl. No. 60/735,458, filed Nov. 11, 2005, Murphy et al.
U.S. Appl. No. 60/764,508, filed Feb. 2, 2006, Murphy et al.
Petition for Inter Partes Review of U.S. Pat. No. 8,384,771. including Exhibits 1001-1012 and 1020-1022; Case No. IPR2021-00647, filed Mar. 23, 2021 (808 pages).

(56) References Cited

OTHER PUBLICATIONS

Documents filed with *Microsoft Corporation v. D3D Technologies, Inc.*; United States Patent and Trademark Office—Before the Patent Trial and Appeal Board, Case No. IPR2021-00647; Filed on Mar. 26, 2021 (5 pages).
Petition for inter Partes Review of U.S. Pat. No. 9,349,183, including Exhibits 1001-1007,1009; 1010; 1013; 1014, and 1020-1022; Case No. IPR2021-00648, filed Mar. 23, 2021 (1,020 pages).
Documents filed with *Microsoft Corporation v. D3D Technologies, Inc.*; United States Patent and Trademark Office—Before the Patent Trial and Appeal Board, Case No. IPR2021-00648; Filed on Mar. 26, 2021 (5 pages).

\* cited by examiner

METHOD AND APPARATUS FOR PERFORMING STEREOSCOPIC ROTATION OF A VOLUME ON A HEAD DISPLAY UNIT

CROSS REFERENCE TO RELATED APPLICATIONS

This application is a Continuation of U.S. patent application Ser. No. 16/506,073, filed Jul. 9, 2020, which is a Continuation of U.S. patent application Ser. No. 15/878,463, filed Jan. 24, 2018, now U.S. Pat. No. 10,795,457, which is a Continuation-in-Part of U.S. patent application Ser. No. 14/877,442, filed Oct. 7, 2015, now U.S. Pat. No. 9,980,691, which is a Continuation-in-Part of U.S. patent application Ser. No. 12/176,569, filed Jul. 21, 2008, now U.S. Pat. No. 9,349,183, which is a Continuation-in-Part of U.S. patent application Ser. No. 11/941,578, filed Nov. 16, 2007, now U.S. Pat. No. 8,384,771, which claims the benefit of and priority under 35 U.S.C. § 119(e) to U.S. Patent Application No. 60/877,931, filed Dec. 28, 2006, each of which are incorporated herein by reference in their entirety.

TECHNICAL FIELD

Aspects of this disclosure are generally related to radiological imaging, and more particularly to blood vessel appearance using extended reality headsets.

BACKGROUND

One of the challenges that physicians face when viewing a volume with an augmented reality, virtual reality or mixed reality headset is visualization of blood flow.

SUMMARY

All examples, aspects and features mentioned in this document can be combined in any technically possible way.

In accordance with some implementations a method of denoting blood flow within a 3D volume on a head display unit (HDU), comprises: generating a 3D volumetric dataset containing at least one blood vessel; generating at least one pointer; determining the direction of blood flow; modifying the 3D volumetric dataset by placing the at least one pointer in proximity to the at least one blood vessel in a direction aligned with a direction of blood flow; displaying, in said HDU, a left eye image based on said modified 3D volumetric dataset and a right eye image based on said modified 3D volumetric dataset, wherein said left eye image and said right eye image are alternate three-dimensional images; and displaying, in said HDU, the at least one pointer advancing in the direction of blood flow. In some implementations placing the at least one pointer in proximity to the at least one blood vessel comprises placing a 2D arrow. In some implementations placing the at least one pointer in proximity to the at least one blood vessel comprises placing a 3D arrow. Some implementations comprise displaying, in said HDU, the pointer with changing color. Some implementations comprise displaying, in said HDU, the pointer advancing in the direction of blood flow faster in arteries than veins.

BRIEF DESCRIPTION OF FIGURES

The patent or application file contains at least one drawing executed in color. Copies of this patent or patent application publication with color drawing(s) will be provided by the Office upon request and payment of the necessary fee.

DETAILED DESCRIPTION OF FIGURES

Some aspects, features and implementations described herein may include machines such as computers, electronic components, radiological components, optical components, and processes such as computer-implemented steps. It will be apparent to those of ordinary skill in the art that the computer-implemented steps may be stored as computer-executable instructions on a non-transitory computer-readable medium. Furthermore, it will be understood by those of ordinary skill in the art that the computer-executable instructions may be executed on a variety of tangible processor devices. For ease of exposition, not every step, device or component that may be part of a computer or data storage system is described herein. Those of ordinary skill in the art will recognize such steps, devices and components in view of the teachings of the present disclosure and the knowledge generally available to those of ordinary skill in the art. The corresponding machines and processes are therefore enabled and within the scope of the disclosure.

Figure 1:
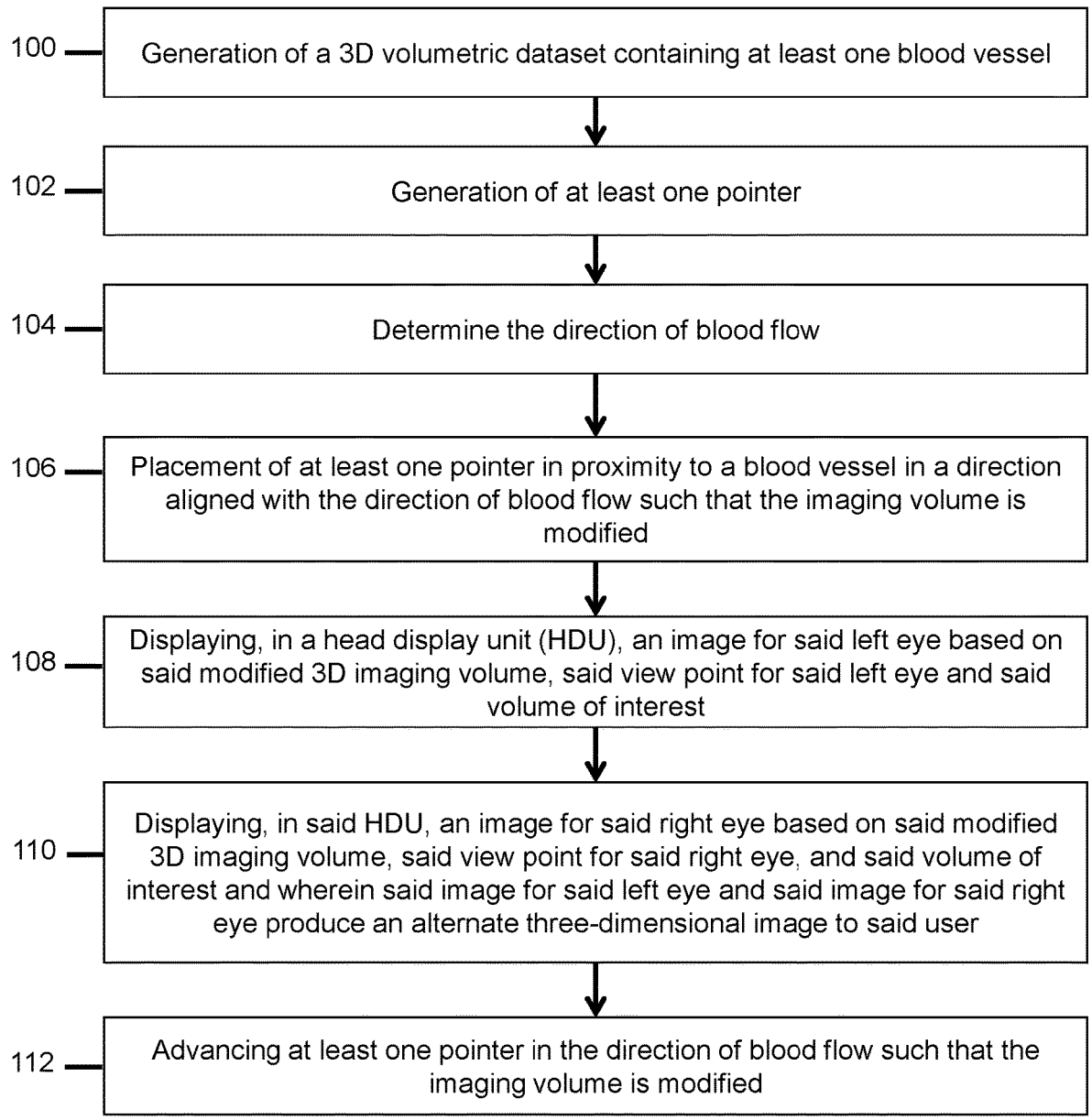
FIG. 1 illustrates the method for using pointers to denote blood flow direction within a 3D volumetric dataset and viewing with a head display unit.

FIG. 1 illustrates an implementation of a method for using pointers to denote blood flow direction within a 3D volumetric dataset and viewing with a head display unit. In the first step 100, a 3D volumetric dataset containing at least one blood vessel is generated. In the second step 102, at least one pointer is generated. In the third step 104, the direction of blood flow is determined. In the fourth step 106, at least one pointer in proximity to a blood vessel in a direction aligned with the direction of blood flow is placed such that the 3D volumetric dataset is modified. In the fifth step 108, an image for said left eye based on said modified 3D imaging volume, said view point for said left eye and said volume of interest is displayed, in the left eye display of the said HDU. In the sixth step 110, an image for said right eye based on said modified 3D imaging volume, said view point for said right eye, and said volume of interest and wherein said image for said left eye and said image for said right eye produce an alternate three-dimensional image to said user. In the seventh step 112, at least point pointer is advanced in the direction of blood flow such that the imaging volume is modified. Some portions of this process can be repeated such that multiple modified 3D imaging volumes are created and displayed on the HDU. This would serve to provide the visualization of moving arrows and help the imager better understand blood flow.

Figure 2:
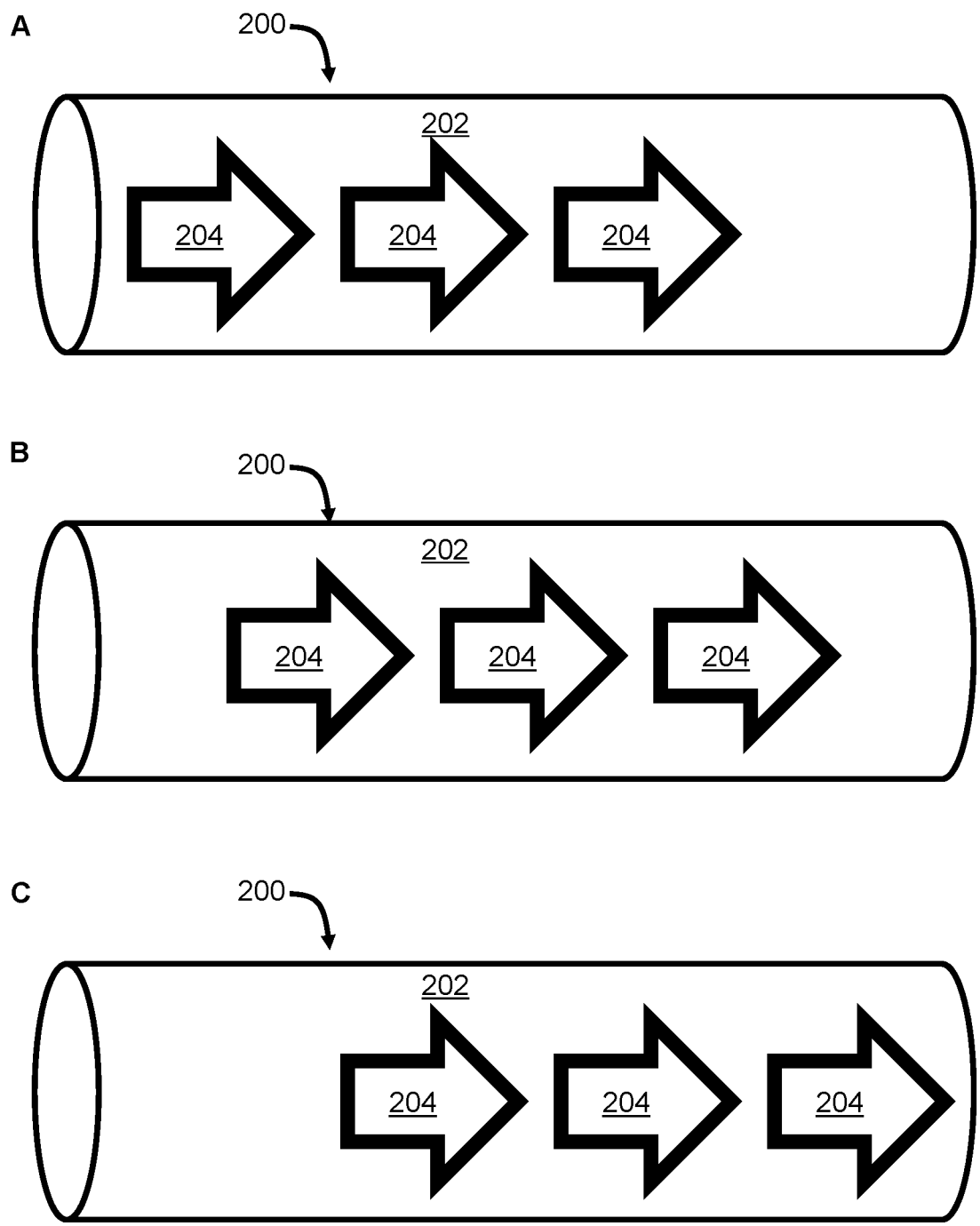
FIG. 2 illustrates advancing pointers to depict the direction of the blood flow.

FIG. 2 illustrates advancing pointers (or arrows) to depict the direction of the blood flow. In the human body, it is common for blood in most arteries to be directed away from the heart and for blood in most veins to be directed towards the heart. However, in some situations in the body (e.g., subclavian steal with retrograde flow in the vertebral artery), this rule does not apply. It can be difficult for even an experienced imager to readily determine which structures are arteries and which structures are veins. Additionally, even if an imager is able to identify a structure as an artery, it can be difficult to determine its orientation without carefully tracing it back to its origin. Through advances in computer processing, these vessels and the direction of blood flow therein can be determined. An effective visual representation method is required. In this method, advancing pointers along an artery can be performed to indicate the direction of blood flow. Similarly, advancing pointers can be performed in a vein. The color of the pointers can be changed to designate to the user whether it is an artery or vein. Further, the rate of advance of the pointers can also be varied, such as to match the natural blood flow rate for a realistic understanding of the hemodynamics of the patient. The pointers could be located in close proximity to (or within the blood vessels, such as within the center of the blood vessel). As a blood vessel curves through the 3D volume space, the path of the pointers would also curve to match that of the normal blood flow. In FIG. 2A, the pointers 204 are shown within the blood vessel lumen 202 in an initial position with respect to the blood vessel wall 200 and position of the remainder of structures within the imaging volume, which are not shown. This would represent the appearance of the imaging volume at an initial time point. In FIG. 2B, the pointers 204 are shown within the blood vessel lumen 202 in an second, slightly advanced position with respect to the blood vessel wall 200 and position of the remainder of structures within the imaging volume, which are not shown. This would represent the appearance of the imaging volume at a subsequent time point. In FIG. 2C, the pointers 204 are shown within the blood vessel lumen 202 in an third, even further advanced position with respect to the blood vessel wall 200 and position of the remainder of structures within the imaging volume, which are not shown. This would represent the appearance of the imaging volume at an additional subsequent time point. The volume that would displayed to the user on an extended reality (i.e., augmented reality, mixed reality or virtual reality headset) would therefore be dynamic and change over time. Even if the user were looking at a particular structure without moving his or her head, some items within the 3D volume would appear to be moving.

Figure 3:
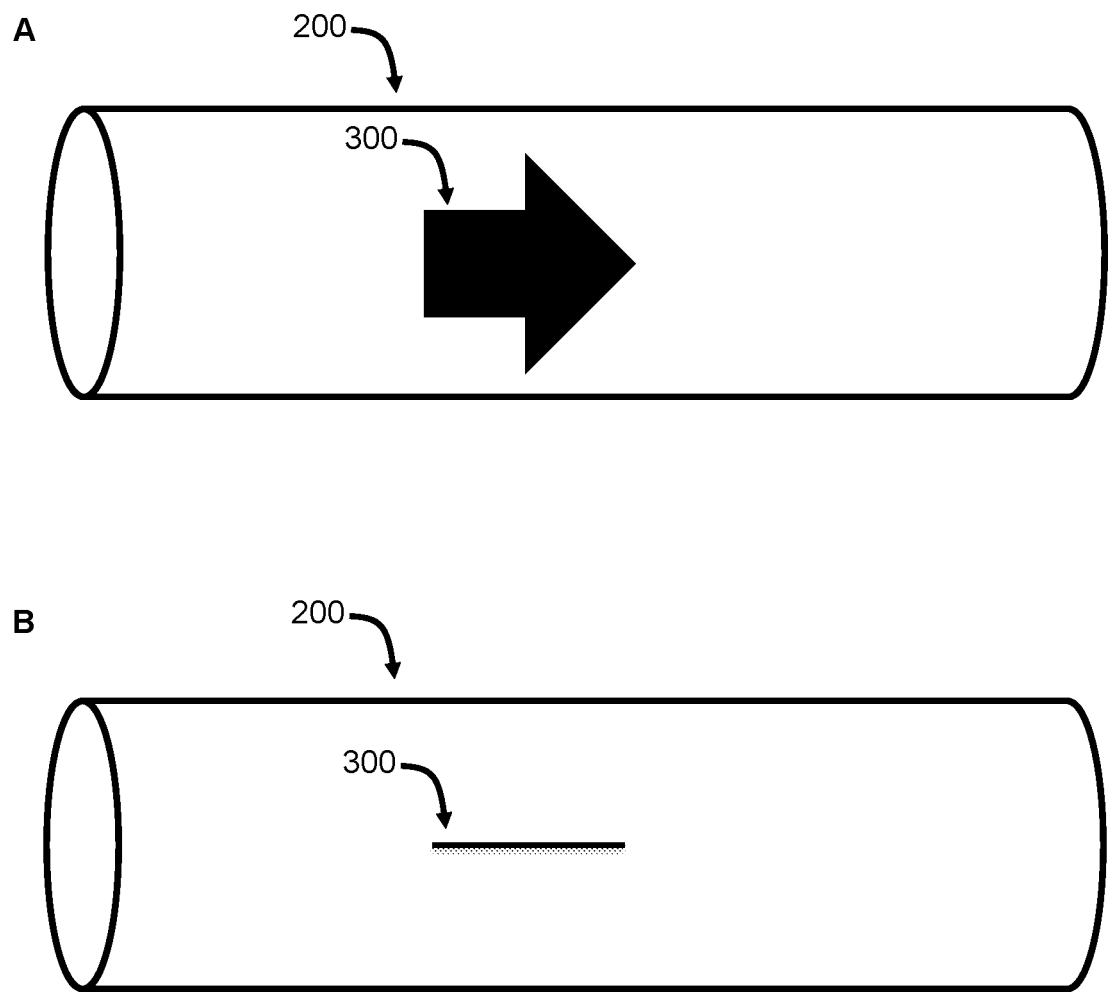
FIG. 3 illustrates placement of a 2D pointer into the 3D volume.

FIG. 3 illustrates placement of a 2D pointer into the 3D volume. In FIG. 3A, a 2D pointer 300 is placed into the blood vessel 200 within the 3D imaging volume. Note that this image illustrates a side view wherein the user's left and right eye view points and left and right eye viewing angles show the side of the 2D pointer 300 and the side of the blood vessel 200 within the 3D volume. In FIG. 3B, the 2D pointer 300 is placed into the blood vessel 200 within the 3D volume. Note that this image illustrates a top down view wherein the user's left and right eye view points and left and right eye viewing angles show the 2D pointer 300 and the top of the blood vessel 200 within the 3D volume. Note that since the 2D pointer is a planar slice, it nearly disappears when viewing from a near top position. A true top position with a planar 2D slice would completely disappear unless the 2D arrow was reoriented. Non-planar slices could also be used, which would be seen from any viewing angle and could be beneficial for viewing direction of blood on a curved vessel.

Figure 4:
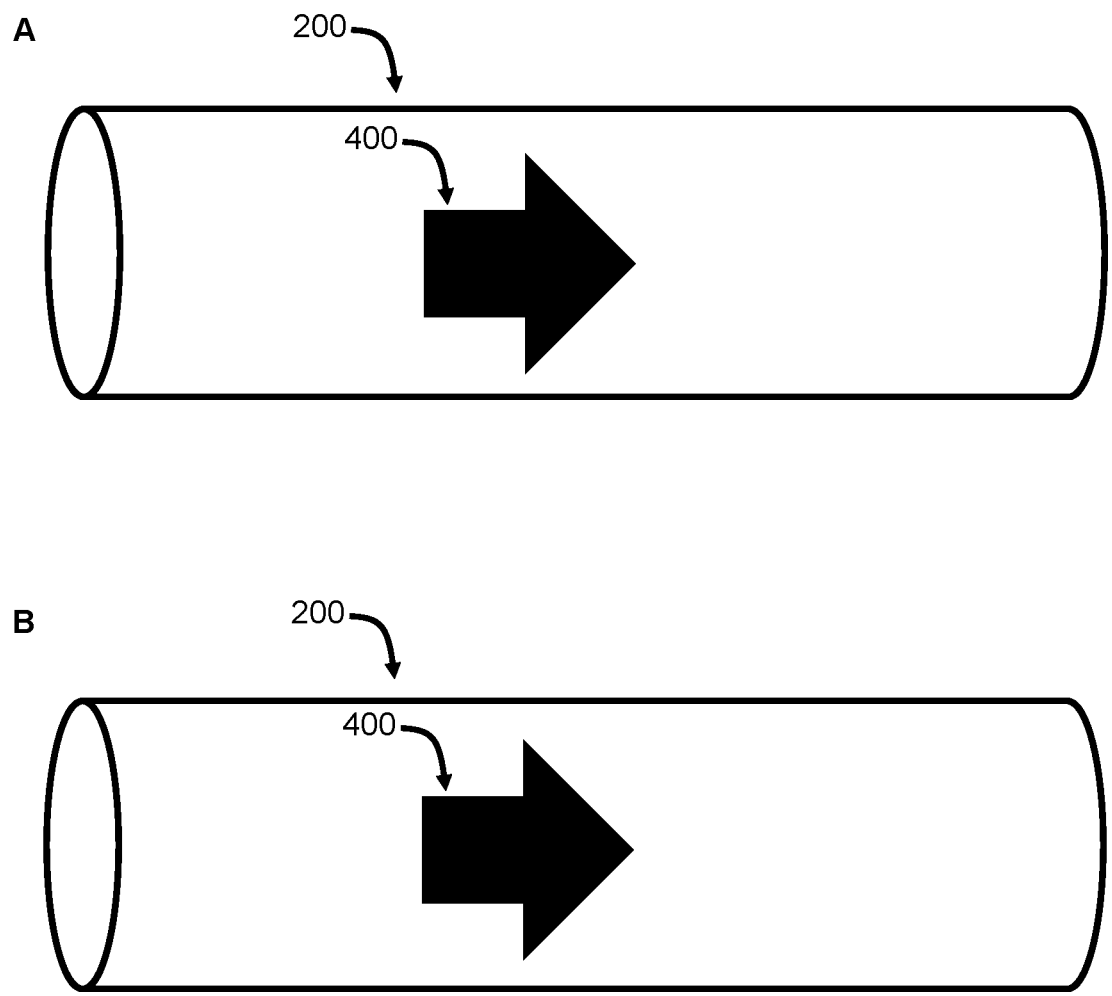
FIG. 4 illustrates placement of a 3D pointer into the 3D volume.

FIG. 4 illustrates placement of a 3D pointer into the 3D volume. In FIG. 4A, a 3D pointer 400 is placed into the blood vessel 200 within the 3D imaging volume. Note that this image illustrates a side view wherein the user's left and right eye view points and left and right eye viewing angles show the side of the 3D pointer 400 and the side of the blood vessel 200 within the 3D volume. In FIG. 4B, the 3D pointer 400 is placed into the blood vessel 200 within the 3D volume. Note that this image illustrates a top down view wherein the user's left and right eye view points and left and right eye viewing angles show the 3D pointer 400 and the top of the blood vessel 200 within the 3D volume. Note that since the pointer is 3D, it is clearly visualized when viewing from a near top position. Such a pointer could be constructed by arranging a series of 2D non-planar slices to form a cone abutting a cylinder (also made of combination of planar and non-planar slices) yielding a 3D pointer 400. By inserting this into the 3D volume, the volume would be modified.

Figure 5:
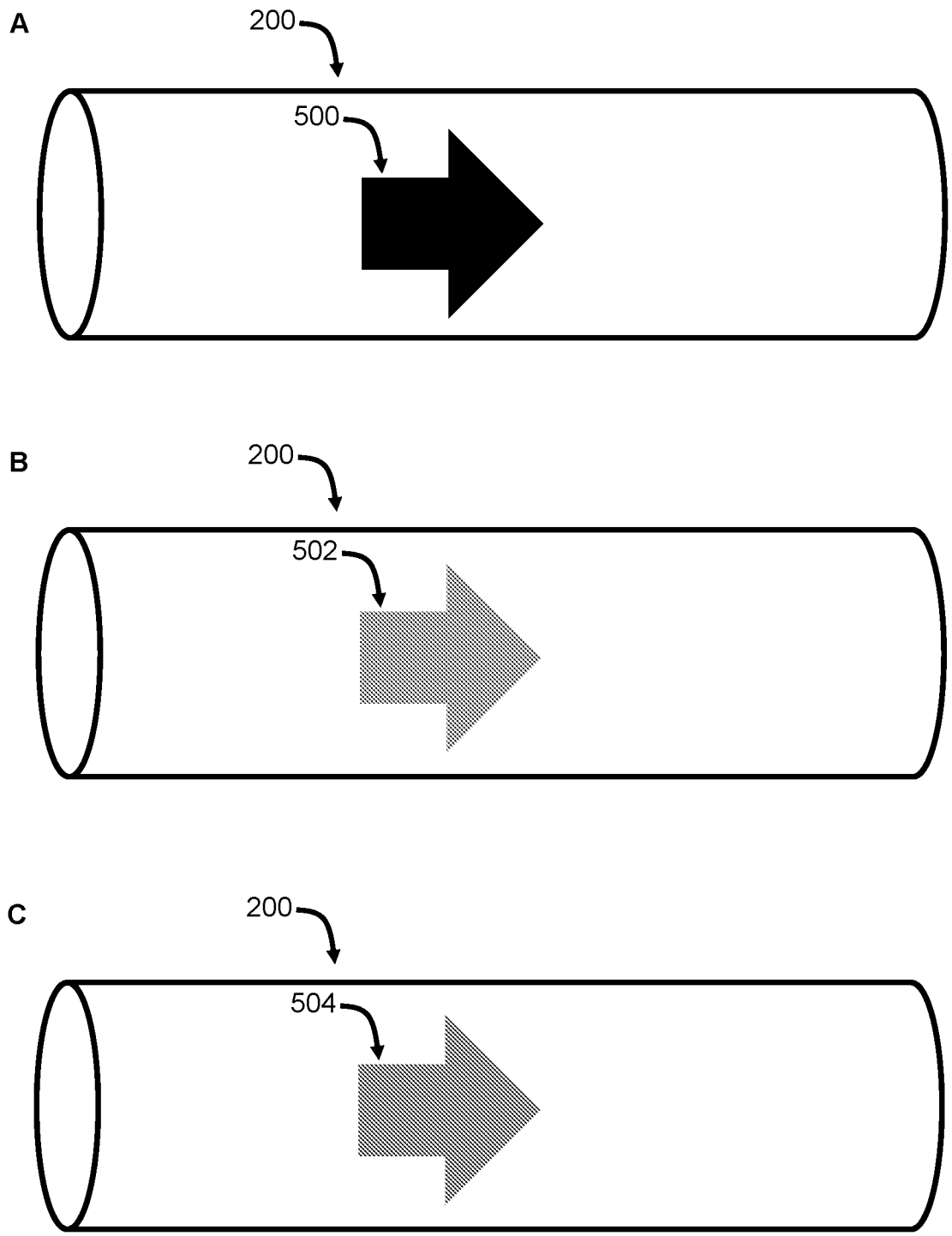
FIG. 5 illustrates placement of a 3D pointer into the 3D volume wherein the appearance of the 3D pointer can be modified.

FIG. 5 illustrates placement of a 3D pointer into the 3D volume wherein the appearance of the 3D pointer can be modified. In FIG. 5A, a 3D pointer 500 is placed into the blood vessel 200 within the 3D volume. Note that the appearance of the 3D pointer 500 is black. In FIG. 5B, the 3D pointer 502 is placed into the blood vessel 200 within the 3D volume. Note that the appearance of the 3D pointer 502 is gray. In FIG. 5C, a 3D pointer 504 is placed into the blood vessel 200 within the 3D volume. Note that the appearance of the 3D pointer 504 is red. Note that the appearance of the pointer can vary. It can be 2D or 3D. It can be a wide range of colors. It can be a wide range of shapes. It can have a wide range of textures.

Figure 6:
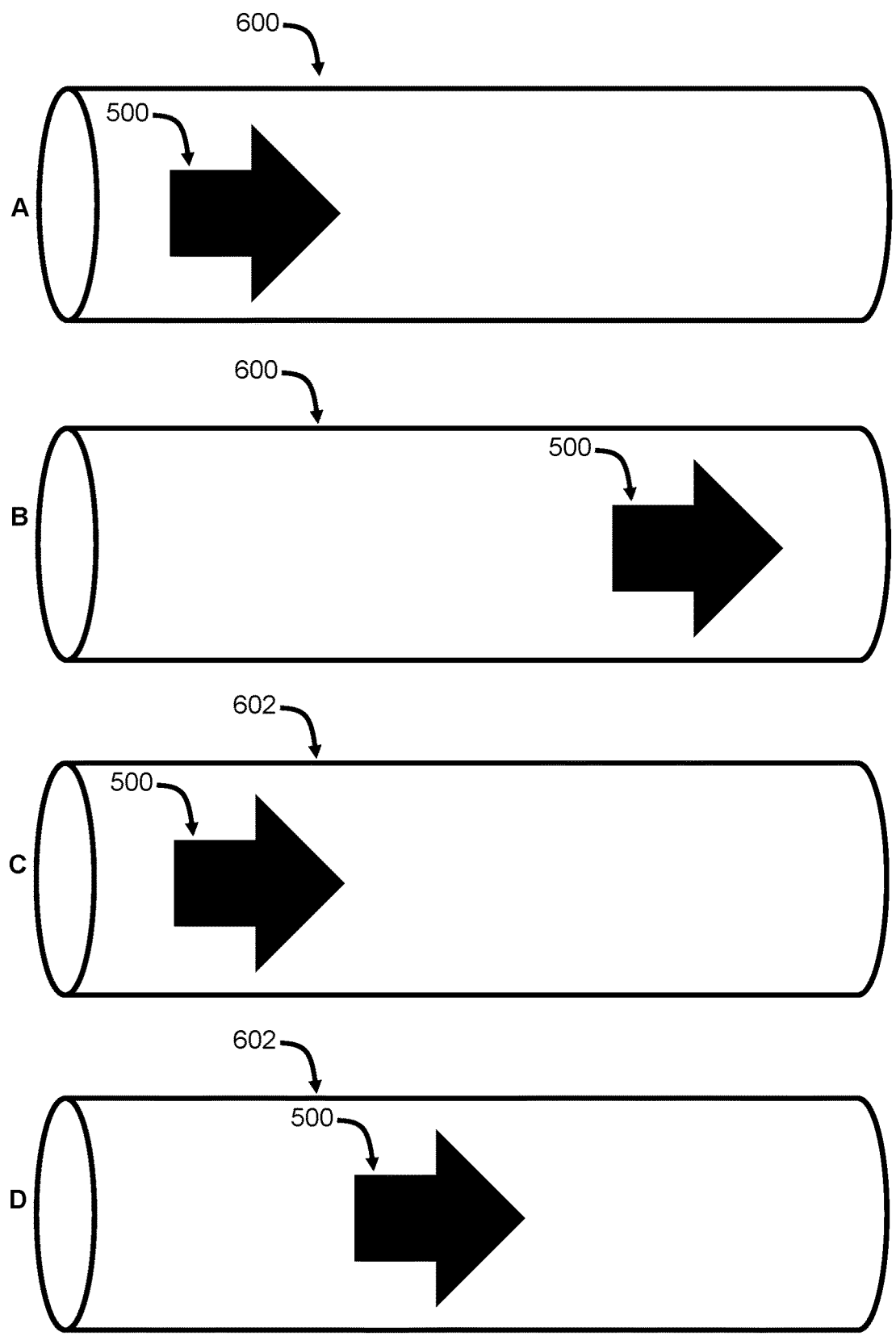
FIG. 6 illustrates variable pointer rates of movement.

FIG. 6 illustrates variable pointer rates of movement. In FIG. 6A, the black 3D pointer 500 is located within the proximal portion of an artery 600 at time point=x. In FIG. 6B, the black 3D pointer 500 has moved and is located distally towards the end of the artery 600 at time point=x+n. In FIG. 6C, the pointer 500 is located within the distal portion of a vein 602 at time point=x. In FIG. 6D, the pointer 500 is located with the mid portion of the vein 602 at time point=x+n. Note that the 3D pointer 500 is moving faster in the artery 600 as compared to the vein 602.

Several features, aspects, embodiments, and implementations have been described. Nevertheless, it will be understood that a wide variety of modifications and combinations may be made without departing from the scope of the inventive concepts described herein. Accordingly, those modifications and combinations are within the scope of the following claims.

What is claimed:

1. A method to display three-dimensional images comprising:
   receiving a volume of interest from a volumetric dataset wherein said volume of interest has a first orientation;
   receiving an initial viewing angle of said volume of interest;
   receiving a first viewpoint for a left eye;
   receiving a second viewpoint for a right eye,
      wherein said first viewpoint and said second viewpoint are different viewpoints;
   displaying, in a head display unit (HDU), a first image for said left eye based on said initial viewing angle, said first viewpoint for said left eye and said volume of interest;
   displaying, in said HDU, a second image for said right eye based on said initial viewing angle, said second viewpoint for said right eye, and said volume of interest, and wherein said first image for said left eye and said second image for said right eye display a three-dimensional image in said HDU;
   receiving a reoriented volume of interest
      wherein said reoriented volume of interest has a second orientation, and wherein said second orientation is different from said first orientation;

displaying, in said HDU, a third image for said left eye based on said initial viewing angle, said first viewpoint for said left eye, and said reoriented volume of interest; and displaying, in said HDU, a fourth image for said right eye based on said initial viewing angle, said second viewpoint for said right eye, and said reoriented volume of interest, and wherein said third image for said left eye and said fourth image for said right eye display an alternate three-dimensional image in said HDU.

2. The method of claim 1, further comprising wherein said third image and said fourth image are filtered.

3. The method of claim 1, further comprising wherein said third image and said fourth image are colored.

4. The method of claim 1, further comprising
wherein a first convergence point is used for said first image and said second image,
wherein a second convergence point is used for said third image and said fourth image, and
wherein said first convergence point and said second convergence point are different.

5. The method of claim 1, further comprising wherein said first viewpoint for said left eye and said second viewpoint for said right eye are stored.

6. The method of claim 1, further comprising wherein said volumetric dataset is generated by an imaging device.

7. The method of claim 1, further comprising implementing automatic rotation of said volume of interest.

8. A method comprising:
configuring a head display unit (HDU) to display stereoscopic images of a volume with rotation wherein:
at a first time point, said HDU displays a first left eye image on a left eye display and a first right eye image on a right eye display;
wherein said volume has a first orientation,
wherein said left eye display of said HDU is configured to be positioned over a left eye of a user,
wherein said first left eye image is generated based on a left eye viewpoint, an initial viewing angle, and said volume,
wherein said first right eye display of said HDU is configured to be positioned over a right eye of said user,
wherein said first right eye image is generated based on a right eye viewpoint, said initial viewing angle, and said volume,
wherein said right eye viewpoint is different from said left eye viewpoint; and
at a subsequent time point, said HDU displays a second left eye image on said left eye display and a second right eye image on said right eye display;
wherein said volume is reoriented from said first orientation at said first time point to a second orientation at said subsequent time point,
wherein said second orientation is different from said first orientation,
wherein said reorientation of said volume is in accordance with an alternate viewing angle,
wherein said second left eye image is generated based on said left eye viewpoint, said alternate viewing angle, and said reoriented volume, and
wherein said second right eye image is generated based on said right eye viewpoint, said alternate viewing angle, and said reoriented volume.

9. The method of claim 8, further comprising wherein said second left eye image and said second right eye image are filtered.

10. The method of claim 8, further comprising wherein said second left eye image and said second right eye image are colored.

11. The method of claim 8, further comprising wherein a first convergence point is used for said first left eye image, said first right eye image, said second left eye image and said second right eye image.

12. The method of claim 8, further comprising wherein said left eye viewpoint, said right eye viewpoint, said initial viewing angle, said first orientation, said alternative viewing angle and said second orientation are stored.

13. The method of claim 8, further comprising wherein said volumetric dataset is generated by an imaging device.

14. The method of claim 8, further comprising implementing automatic rotation of said volume.

15. A system comprising:
a memory;
a processor;
a communications interface;
an interconnection coupling the memory, the processor and the communications interface; and
wherein the memory is encoded with an application for displaying three-dimensional images in a head display unit, that when performed on the processor, provides a process for processing information, the process causing the system to perform the operations of:
using a volumetric dataset;
using a volume of interest from said volumetric dataset wherein said volume of interest had a first orientation;
using an initial viewing angle of said volume of interest;
using a first viewpoint for a left eye;
using a second viewpoint for a right eye, wherein said first viewpoint and said second viewpoint are different viewpoints;
displaying, in a head display unit (HDU), a first image for said left eye based on said initial viewing angle, said first viewpoint for said left eye and said volume of interest;
displaying, in said HDU, a second image for said right eye based on said initial viewing angle, said second viewpoint for said right eye, and said volume of interest, and wherein said first image for said left eye and said second image for said right eye display a three-dimensional image in said HDU;
using an alternate viewing angle;
using a reoriented volume of interest
wherein said reoriented volume of interest has a second orientation,
wherein said second orientation is different from said first orientation, and
wherein said second orientation is reoriented in accordance with said alternate viewing angle;
displaying, in said HDU, a third image for said left eye based on said alternate viewing angle, said first viewpoint for said left eye, and said reoriented volume of interest; and
displaying, in said HDU, a fourth image for said right eye based on said alternate viewing angle, said second viewpoint for said right eye, and said reoriented volume of interest, and wherein said third image for said left eye and said fourth image for said right eye display an alternate three-dimensional image in said HDU.

16. The method of claim 15, further comprising wherein said third image for said left eye and said fourth image for said right eye are filtered.

17. The method of claim 15, further comprising wherein said third image for said left eye and said fourth image for said right eye are colored.

18. The method of claim 15, further comprising
wherein a first convergence point is used for said first image and said second image,
wherein a second convergence point is used for said third image and said fourth image, and
wherein said first convergence point and said second convergence point are different.

19. The method of claim 15, further comprising wherein said first viewpoint for said left eye, said second viewpoint for said right eye, said initial viewing angle, said alternate viewing angle, said first orientation and said second orientation are stored.

20. The method of claim 15, further comprising wherein said volumetric dataset is generated by an imaging device.

21. The method of claim 15, further comprising implementing automatic rotation of said volume of interest.

\* \* \* \* \*